(12) United States Patent
Rafalski et al.

(10) Patent No.: US 6,346,403 B1
(45) Date of Patent: Feb. 12, 2002

(54) METHIONINE METABOLIC ENZYMES

(75) Inventors: J. Antoni Rafalski, Wilmington; Layo O. Famodu, Newark, both of DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/392,772

(22) Filed: Sep. 7, 1999

Related U.S. Application Data

(60) Provisional application No. 60/099,519, filed on Sep. 8, 1998.

(51) Int. Cl.[7] .............................. C12N 9/00; C12N 9/12; C12N 9/88; C12N 1/20; C07H 21/04; A01H 1/00

(52) U.S. Cl. ........................ 435/183; 435/194; 435/232; 435/252.3; 435/320.1; 536/23.2; 530/300; 530/350; 800/278; 800/295

(58) Field of Search ................................. 435/183, 194, 435/232, 252.3, 320.1; 536/23.2; 530/300, 350; 800/278, 295

(56) References Cited

PUBLICATIONS

Sequence alignments of SEQ ID No: 1, 3 & 11 with Accession No. AE000315, D13755 & D62002.*
Jakubowski (1996) Biochemistry 35:8252–8259.
Lee et al. (1991) J. Biol. Chem. 266:18012–18017.
NCBI General Identifier No. 485595.
Plant Mol. Biol. 26, 1085–1101 (1994).
NCBI General Identifier No. 569773.
NCBI General Identifier No. 571553.
NCBI General Identifier No. 3107255.
NCBI General Identifier No. 4292436.
NCBI General Identifier No. 4313709.
NCBI General Identifier No. 4573024.
NCBI General Identifier No. 4966952.
NCBI General Identifier No. 5018236.
NCBI General Identifier No. 5055738.
NCBI General Identifier No. 5555461.
NCBI General Identifier No. 5606916.
NCBI General Identifier No. 5649988.
NCBI General Identifier No. 5666614.
NCBI General Identifier No. 3860247.
NCBI General Identifier No. 1788589.
Science 277 (5331), 1453–1474 (1997).
NCBI General Identifier No. 4091008.
NCBI General Identifier No. 2266985.
Proc. Natl. Acad. Sci. 95(18), 11014–11019.
Archambault de Vencay (1989) Eur. J. Biochem. 182:37–43.
Blanquet et al. (1984) Methods Enzymol. 106:141–152.

* cited by examiner

Primary Examiner—Tekchend Saidha

(57) ABSTRACT

This invention relates to an isolated nucleic acid fragment encoding a methionine metabolic enzyme. The invention also relates to the construction of a chimeric gene encoding all or a portion of the methionine metabolic enzyme, in sense or antisense orientation, wherein expression of the chimeric gene results in production of altered levels of the methionine metabolic enzyme in a transformed host cell.

12 Claims, 1 Drawing Sheet

Figure 1:
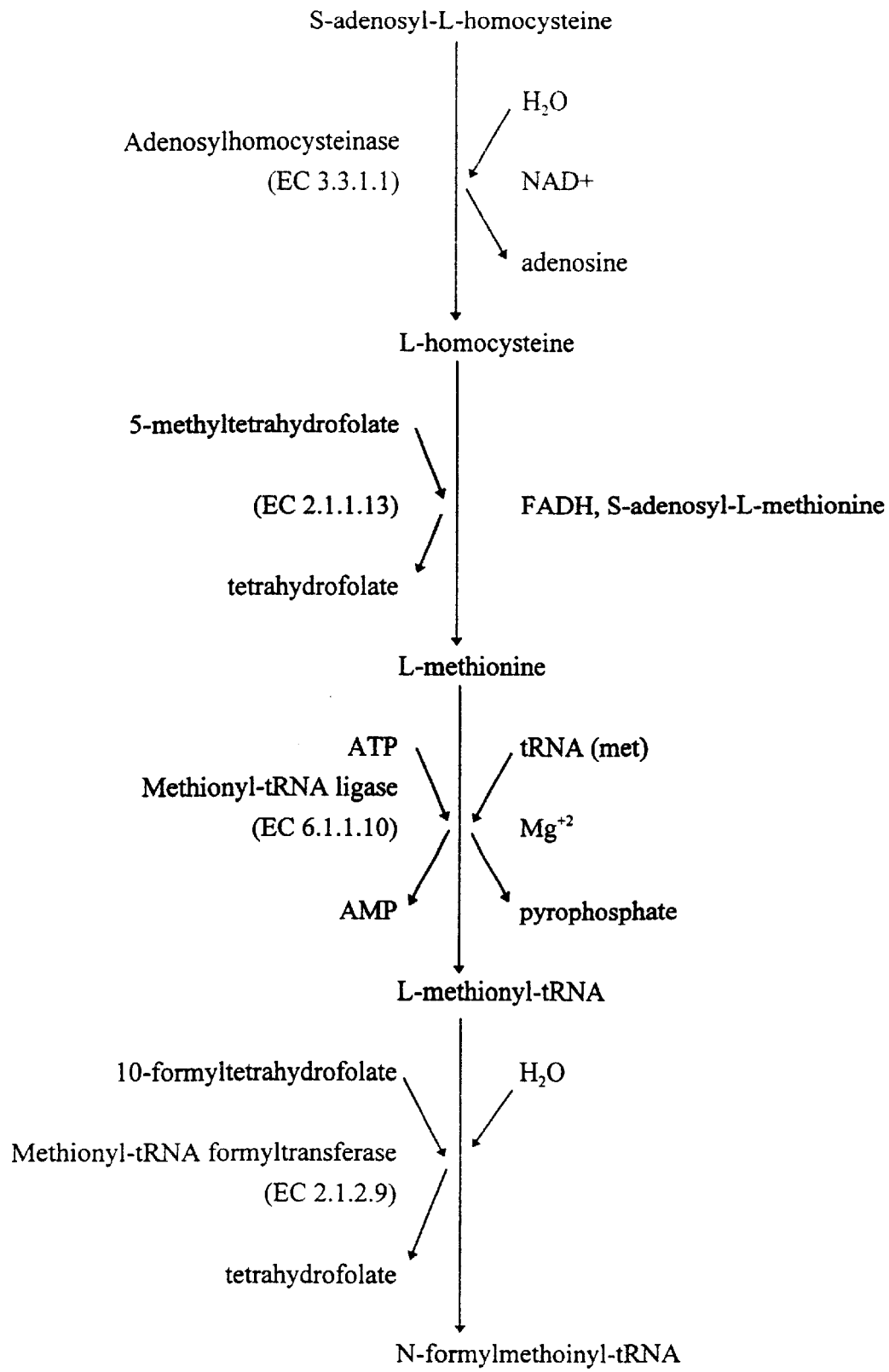

ID NO:10, and a soybean methionyl-tRNA synthetase of

METHIONINE METABOLIC ENZYMES

This application claims priority benefit of U.S. Provisional Application No. 60/099,519 filed Sep. 8, 1998, now pending.

FIELD OF THE INVENTION

This invention is in the field of plant molecular biology. More specifically, this invention pertains to nucleic acid fragments encoding enzymes involved in methionine metabolism in plants and seeds.

BACKGROUND OF THE INVENTION

Human food and animal feed derived from many grains are deficient in the sulfur amino acids, methionine and cysteine, which are required in an animal diet. In corn, the sulfur amino acids are the third most limiting amino acids, after lysine and tryptophan, for the dietary requirements of many animals. The use of soybean meal, which is rich in lysine and tryptophan, to supplement corn in animal feed is limited by the low sulfur amino acid content of the legume. Thus, an increase in the sulfur amino acid content of either corn or soybean would improve the nutritional quality of the mixtures and reduce the need for further supplementation through addition of more expensive methionine.

One genetic engineering approach to increase the sulfur amino acid content of seeds is to isolate genes coding for proteins that are rich in the sulfur-containing amino acids methionine and cysteine, to link the genes to strong seed-specific regulatory sequences, to transform the chimeric gene into crops plants and to identify transformants wherein the gene is sufficiently highly expressed to cause an increase in total sulfur amino acid content. However, increasing the sulfur amino acid content of seeds by expression of sulfur-rich proteins may be limited by the ability of the plant to synthesize methionine, by the synthesis and stability of the methionine-rich protein, and by effects of over-accumulation of the methionine-rich protein on the viability of the transgenic seeds.

An alternative approach would be to increase the production and accumulation of the free amino acid, methionine, via genetic engineering technology. However, little guidance is available on the control of the biosynthesis and accumulation of methionine in plants, particularly in the seeds of plants.

Methionine-tRNA ligase (EC 6.1.1.10), also called Methionyl-tRNA synthetase, or L-Methione:tRNA(Met) ligase (AMP-forming) belongs to the class-I aminoacyl-tRNA synthetases. This is a cytoplasmic enzyme which catalyzes the ligation of methionine to transfer RNA in protein translation. Methionine-tRNA ligase is the first enzyme sustaining the methionine pathway in translation initiation in *Escherichia coli*. This enzyme is probably essential for cell survival, being required not only for elongation of protein synthesis but also for the initiation of all mRNA translation through initiator tRNA-aminoacylation. The active site of methionyl-tRNA synthetase possesses two functions: synthetic, which provides Met-tRNA for protein synthesis, and editing, which rejects inadvertently misactivated homocysteine. During editing, the side chain —SH group of homocysteine reacts with its activated carboxyl group forming a cyclic thioester, homocysteine thiolactone. There is a specific —SH binding subsite, distinct from the methionine binding subsite, in the synthetic/editing active site of methionyl-tRNA synthetase (Jakubowski (1996) *Biochemistry* 35:8252–8259).

Methionyl-tRNA formyltransferase (10-formyltetrahydrofolate:L-methionyl-tRNA N-transformylase, EC 2.1.2.9) produces formylmethionyl-tRNA. This residue, which already has an amide bond, is the first residue in a polypeptide which initiates with methionine. The structure and/or sequence of the first three base pairs at the end of the amino acid acceptor stem of *Escherichia coli* initiator tRNA and the discriminator base 73 are important for its formylation by *E. coli* methionyl-tRNA transformylase. Changes in the rest of the acceptor stem, dihydrouridine stem, anticodon stem, anticodon sequence, and T psi C stem have little or no effect on formylation (Lee et al. (1991) *J. Biol. Chem.* 266:18012–18017). Corn, Rice and Soybean ESTs encoding polypeptides with similarities to methionyl-tRNA formyltransferase are found in the NCBI database having General Identifier Nos. 485595, 569773, 571553, 3107255, 4292436 4313709, 4573024, 4966952, 5018236, 5055738, 5555461, 5606916, 5649988 and 5666614.

SUMMARY OF THE INVENTION

The present invention relates to isolated polynucleotides comprising a nucleotide sequence encoding a first polypeptide of at least 500 amino acids having at least 90% identity, preferably at least 400 amino acids having at least 95% identity, based on the Clustal method of alignment when compared to a polypeptide selected from the group consisting of a corn methionyl-tRNA fomyltransferase of SEQ ID NO:2, a rice methionyl-tRNA formyltransferase of SEQ ID NO:4, a soybean methionyl-tRNA formyltransferase of SEQ ID NO:6, a wheat methionyl-tRNA formyltransferase of SEQ ID NO:8, a corn methionyl-tRNA synthetase of SEQ ID NO:10, and a soybean methionyl-tRNA synthetase of SEQ ID NO:12. The present invention also relates to an isolated polynucleotide comprising the complement of the nucleotide sequences described above. It is preferred that the isolated polynucleotides of the claimed invention comprise a nucleic acid sequence selected from the group consisting of SEQ ID NOs:1, 3, 5, 7, 9 and 11 that codes for the polypeptide selected from the group consisting of SEQ ID NOs:2, 4, 6, 8, 10 and 12. The present invention also relates to an isolated polynucleotide comprising a nucleotide sequences of at least 40 (preferably at least 30) contiguous nucleotides derived from a nucleotide sequence selected from the group consisting of SEQ ID NOs:1, 3, 5, 7, 9, 11 and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eucaryotic, such as a yeast or a plant cell, or procaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to a methionyl-tRNA formyltransferase or a methionyl-tRNA synthetase polypeptide of at least 500 amino acids having at least 90% homology, preferably at least 400 amino acids having at least 95% homology, based on the Clustal method of alignment compared to a polypeptide selected from the group consisting of SEQ ID NOs:2, 4, 6, 8, 10 and 12.

The present invention relates to a method of selecting an isolated polynucleotide that affects the level of expression of a methionyl-tRNA formyltransferase or a methionyl-tRNA synthetase polypeptide in a plant cell, the method comprising the steps of:

constructing an isolated polynucleotide or chimeric gene of the present invention;

introducing the isolated polynucleotide into a plant cell;

measuring the level a methionyl-tRNA formyltransferase or a methionyl-tRNA synthetase polypeptide in the plant cell containing the polynucleotide; and comparing the level of a methionyl-tRNA formyltransferase or a methionyl-tRNA synthetase polypeptide in the plant cell containing the isolated polynucleotide with the level of a methionyl-tRNA formyltransferase or a methionyl-tRNA synthetase polypeptide in a plant cell that does not contain the isolated polynucleotide.

The present invention relates to a method of obtaining a nucleic acid fragment encoding a substantial portion of a methionyl-tRNA formyltransferase or a methionyl-tRNA synthetase gene, preferably a plant methionyl-tRNA formyltransferase or methionyl-tRNA synthetase gene, comprising the steps of: synthesizing an oligonucleotide primer comprising a nucleotide sequence of at least 40 (preferably at least 30) contiguous nucleotides derived from a nucleotide sequence selected from the group consisting of SEQ ID NOs: 1, 3, 5, 7, 9, 11 and the complement of such nucleotide sequences; and amplifying a nucleic acid fragment (preferably a cDNA inserted in a cloning vector) using the oligonucleotide primer. The amplified nucleic acid fragment preferably will encode a portion of a thioredoxin polypeptide amino acid sequence.

The present invention also relates to a method of obtaining a nucleic acid fragment encoding all or a substantial portion of the amino acid sequence encoding a to a methionyl-tRNA formyltransferase or a methionyl-tRNA synthetase polypeptide comprising the steps of:

probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

BRIEF DESCRIPTION OF THE DRAWING AND SEQUENCE LISTING

The invention can be more fully understood from the following detailed description and the accompanying Drawing and Sequence Listing which form a part of this application.

FIG. 1 depicts the methionine metabolism biochemical pathway. In the presence of water and NAD$^+$, adenosylhomocysteinase (EC 3.3.1.1) catalyzes the conversion of S-adenosyl-L-homocysteine to adenosine and L-homocysteine. Using FADH, and S-adenosyl-L-methionine as cofactors, methionine synthase (EC 2.1.1.13) catalyzes the conversion of L-homocysteine and 5-methyltetrahydrofolate to L-methionine and tetrahydrofolate. In the presence of Mg$^{+2}$, and using energy from the conversion of ATP to AMP, methionyl tRNA ligase (EC 6.1.1.10) adds tRNA to L-methionine to produce L-methionyl-tRNA and pyrophosphate. Using water as a cofactor, methionyl-tRNA formyltransferase (EC 2.1.2.9) transfers the formyl group from 10-formyltetrahydrofolate to N-methionyl-tRNA and releases tetrahydrofolate.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Methionine Metabolic Enzymes

| Protein | Clone Designation | SEQ ID NO: (Nucleotide) | (Amino Acid) |
|---|---|---|---|
| Corn Methionyl-tRNA Formyltransferase | cen3n.pk0074.d5 | 1 | 2 |
| Rice Methionyl-tRNA Formyltransferase | rca1c.pk007.e16 | 3 | 4 |
| Soybean Methionyl-tRNA Formyltransferase | sml1c.pk007.k24 | 5 | 6 |
| Wheat Methionyl-tRNA Formyltransferase | wl1n.pk0019.b5 | 7 | 8 |
| Corn Methionyl-tRNA Synthetase | p0128.cpibk48r | 9 | 10 |
| Soybean Methionyl-tRNA Synthetase | sgs5c.pk0004.e10 | 11 | 12 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, or synthetic DNA. An isolated polynucleotide of the present invention may include at least 40 contiguous nucleotides, preferably at least 30 contiguous nucleotides, of the nucleic acid sequence of the SEQ ID NOs:1, 3, 5, 7, 9 and 11.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucelic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, a polynucleotide comprising a nucleotide sequence of at least 40 (preferably 30) contiguous nucleotides derived from a nucleotide sequence selected from the group consisting of SEQ ID NOs:1, 3, 5, 7, 9, 11 and the complement of such nucleotide sequences may be used in methods of selecting an isolated polynucleotide that affects the expression of a methionyl-tRNA formyltransferase or a methionyl-tRNA synthetase polypeptide in a plant cell.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (polynucleotides) encode amino acid sequences that are 80% identical to the amino acid sequences reported herein. Preferred nucleic acid fragment encode amino acid sequences that are 85% identical to the amino acid sequences reported herein. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid.

Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual;* Cold Spring Harbor Laboratory Press: Cold Spring Harbor, 1989 (hereinafter "Maniatis").

Nucleic acid fragments encoding at least a portion of several methionine metabolic enzymes have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other methionyl-tRNA formyltransferases or methionyl-tRNA synthetases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least 40 (preferably 30) contiguous nucleotides derived from a nucleotide sequence selected from the group consisting of SEQ ID NOs:1, 3, 5, 7, 9, 11 and the complement of such nucleotide sequences may be used in such methods to obtain a nucleic acid fragment encoding a substantial portion of an amino acid sequence of a methionyl-tRNA formyltransferase or methionyl-tRNA synthetase polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of methionine-containing products in those cells. Because methionyl-tRNA synthetase is essential for cell survival, inhibitors of this enzyme may be herbicidal targets. Manipulation of the methionyl-tRNA synthetase and formylmethionyl-tRNA contents of corn and soybean, among others, may lead to increase methionine content in the seeds of these crops.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded methionine metabolic enzyme. An example of a vector for high level expression of the instant polypeptides in a bacterial host is provided (Example 7).

Additionally, the instant polypeptides can be used as a targets to facilitate design and/or identification of inhibitors of those enzymes that may be useful as herbicides. This is desirable because the polypeptides described herein catalyze various steps in methionine metabolism. Accordingly, inhibition of the activity of one or more of the enzymes described herein could lead to inhibition of plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide,* Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean and wheat tissues were prepared. The characteristics of the libraries are described below.

TABLE 2 cDNA Libraries From Corn, Rice, Soybean and Wheat

| Library | Tissue | Clone |
|---|---|---|
| cen3n | Corn Endosperm 20 Days After Pollination* | cen3n.pk0074.d5 |
| p0128 | Corn Primary and Secondary Immature Ear | p0128.cpibk48r |
| rca1c | Rice Nipponbare callus | rca1c.pk007.e16 |
| sgs5c | Soybean Seeds 4 Days After Germination | sgs5c.pk0004.e10 |
| sml1c | Soybean Mature Leaf | sml1c.pk007.k24 |
| wl1n | Wheat Leaf From 7 Day Old Seedling* | wl1n.pk0019.b5 |

*These libraries were normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding methionine metabolic enzymes were identified by conducting BLAST (Basic Local Alignment Search Tool; Altschul et al. (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Methionyl-tRNA Formyltransferase

The BLASTX search using the EST sequences from clones listed in Table 3 revealed similarity of the polypeptides encoded by the cDNAs to an unknown *Arabidopsis thaliana* protein (NCBI General Identifier No.3860247) and to methionyl-tRNA formyltransferase from *Escherichia coli* (NCBI General Identifier No. 1788589). Shown in Table 3 are the BLAST results for the sequences of the entire cDNA inserts comprising the indicated cDNA clones ("FIS"):

TABLE 3

BLAST Results for Sequences Encoding Polypeptides Homologous to Methionyl-tRNA Formyltransferase

| Clone | Status | BLAST pLog Score | |
|---|---|---|---|
| | | 1788589 | 3860247 |
| cen3n.pk0074.d5 | FIS | 45.40 | 154.0 |
| rca1c.pk007.e16 | FIS | 57.00 | >254.0 |
| sml1c.pk007.k24 | FIS | 48.22 | 168.0 |
| wl1n.pk0019.b5 | FIS | 18.30 | 66.7 |

ESTs encoding polypeptides with similarities to methionyl-tRNA formyltransferase exist in the NCBI database.

From clone cen3n.pk0074.d5:
nucleotides 728 through 1269 are 98% identical to nucleotides 569 through 27 of a 569 nucleotide corn EST having NCBI General Identifier No. 5018236.
nucleotides 852 through 1378 are 98% identical to nucleotides 553 through 28 of a 553 nucleotide corn EST having NCBI General Identifier No. 5055738.
nucleotides 870 through 1378 are 98% identical to nucleotides 383 through 1 of a 383 nucleotide corn EST having NCBI General Identifier No. 4573024.
nucleotides 911 through 1330 are 95% identical to nucleotides 454 through 36 of a 461 nucleotide corn EST having NCBI general Identifier No. 4966952.
nucleotides 511 through 846 are 95% identical to nucleotides 65 through 404 of a 404 nucleotide corn EST having NCBI general Identifier No. 485595.
nucleotides 194 through 463 are 98% identical to nucleotides 126 through 395 of a 395 nucleotide corn EST having NCBI general Identifier No. 5649988.

From clone rca1c.pk007.e16:
nucleotides 211 through 675 are 93% identical to nucleotides 179 through 643 of a 643 nucleotide corn EST having NCBI General Identifier No. 5555461.
nucleotides 6 through 356 are 98% identical to nucleotides 4 through 354 of a 354 nucleotide rice EST having NCBI General Identifier No. 569773.
nucleotides 3 through 363 are 96% identical to nucleotides 4 through 361 of a 380 nucleotide rice EST having NCBI General Identifier No. 571553.
nucleotides 1269 through 1547 are 94% identical to nucleotides 1 through 281 of a 281 nucleotide rice EST having NCBI General Identifier No. 3107255.

From clone sml1c.pk007.k24:
nucleotides 908 through 1338 are 100% identical to nucleotides 440 through 10 of a 440 nucleotide soybean EST having NCBI General Identifier No. 4313709.
nucleotides 188 through 668 are 89% identical to nucleotides 25 through 505 of a 507 nucleotide soybean EST having NCBI General Identifier No. 5606916.
nucleotides 1 through 256 are 100% identical to nucleotides 252 through 507 of a 507 nucleotide soybean EST having NCBI General Identifier No. 5666614.
nucleotides 1 through 249 are 100% identical to nucleotides 214 through 462 of a 462 nucleotide soybean EST having NCBI General Identifier No. 4292436.

The data in Table 4 represents a calculation of the percent identity of the amino acid sequences set forth in SEQ ID NOs:2, 4, 6 and 8 and the *Escherichia coli* sequence (NCBI General Identifier No. 1788589).

TABLE 4

Percent Identity of Amino Acid Sequences Deduced From the Nucleotide Sequences of cDNA Clones Encoding Polypeptides Homologous to Methionyl-tRNA Formyltransferase

| SEQ ID NO. | Percent Identity to 1788589 |
|---|---|
| 2 | 27.3 |
| 4 | 25.8 |
| 6 | 30.7 |
| 8 | 28.1 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a corn, a rice, a soybean and a wheat methionyl-tRNA formyltransferase. These sequences represent variant corn, rice and soybean sequences encoding methionyl-tRNA formyltransferase, and the first wheat sequences encoding methionyl-tRNA formyltransferase.

Example 4

Characterization of cDNA Clones Encoding Methionyl-tRNA Synthetase

The BLASTX search using the EST sequences from clones listed in Table 5 revealed similarity of the polypeptides encoded by the cDNAs to methionyl-tRNA synthetase from *Oryza sativa* and *Arabidopsis thaliana* (NCBI General Identifier Nos. 4091008 and 2266985, respectively). Shown in Table 5 are the BLAST results for individual ESTs ("EST"), the sequences of the entire cDNA inserts comprising the indicated cDNA clones ("FIS"):

TABLE 5

BLAST Results for Sequences Encoding Polypeptides Homologous to Methionyl-tRNA Synthetase

| Clone | Status | NCBI General Identification No. | BLAST pLog Score |
| --- | --- | --- | --- |
| p0128.cpibk48r | FIS | 4091008 | 84.00 |
| sgs5c.pk0004.e10 | EST | 2266985 | 70.52 |

The data in Table 6 represents a calculation of the percent identity of the amino acid sequences set forth in SEQ ID NOs:10 and 12 and the *Oryza sativa* (NCBI General Identifier No. 4091008) and *Arabidopsis thaliana* (NCBI General Identifier No. 2266985) sequences.

TABLE 6

Percent Identity of Amino Acid Sequences Deduced From the Nucleotide Sequences of cDNA Clones Encoding Polypeptides Homologous to Methionyl-tRNA Synthetase

| SEQ ID NO. | Percent Identity | NCBI General Identifier No. |
| --- | --- | --- |
| 10 | 88.5 | 4091008 |
| 12 | 85.5 | 2266985 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a corn and a soybean methionyl-tRNA synthetase. These sequences represent the first corn and soybean sequences encoding methionyl-tRNA synthetase.

Example 5

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/

He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 6

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), SmaI, KpnI and XbaI. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli;* Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 8

Evaluating Compounds for Their Ability to Inhibit the Activity of Methionine Metabolic Enzymes The polypeptides described herein may be produced using any number of methods known to those skilled in the art. Such methods include, but are not limited to, expression in bacteria as described in Example 7, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("$(His)_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a $(His)_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for methionyl-tRNA synthetase are presented by Archambault de Vencay (1989) Eur. J. Biochem. 182:37–43. Assays for methionyl-tRNA formyltransferase are presented by Blanquet et al. (1984) Methods Enzymol. 106:141–152.

What is claimed is:

1. An isolated polynucleotide selected from the group consisting of:
   (a) an isolated polynucleotide that encodes a methionyl-tRNA fomyltransferase polypeptide having a sequence identity of at least 95% when compared to a member selected from the group consisting of SEQ ID NO:2, SEQ ID NO:4, SEQ ID NO:6, SEQ ID NO:8, and
   (b) an isolated polynucleotide that encodes a methionyl-tRNA synthetase having a sequence identity of at least 95% when compared to a member selected from the group consisting of SEQ ID NO:10, and SEQ ID NO:12.

2. The polynucleotide of claim 1 wherein the polynucleotide encodes a polypeptide selected from the group consisting of SEQ ID NO:2, SEQ ID NO:4, SEQ ID NO:6, SEQ ID NO:8, SEQ ID NO:10, SEQ ID NO:12.

3. The polynucleotide of claim 1, wherein the polynucleotide comprises a nucleotide sequence selected from the group consisting of SEQ ID NO:1, SEQ ID NO:3, SEQ ID NO:5, SEQ ID NO:7, SEQ ID NO:9, and SEQ ID NO:11.

4. The polynucleotide of claim 1, wherein the polypeptide is involved in methionine metabolic pathway.

5. The polynucleotide of claim 4, wherein the polypeptide is a methionyl-tRNA formyltransferase.

6. An isolated complement of the polynucleotide of claim 1, wherein (a) the complement and the polynucleotide consist of the same number of nucleotides, and (b) the nucleotide sequences of the complement and the polynucleotide have 100% complementarity.

7. An isolated polynucleotide that (1) encodes a polypeptide having methionyl-tRNA synthetase or methionyl-tRNA fomyltransferase activity, and (2) remains hybridized with the isolated polynucleotide of claim 1 under a wash condition of 0.1×SSC, 0.1% SDS, and 65° C.

8. A cell comprising the polynucleotide of claim 1.

9. A transgenic plant comprising the polynucleotide of claim 1.

10. A method for transforming a cell comprising introducing into a cell the polynucleotide of claim 1.

11. A method for producing a transgenic plant comprising (a) transforming a plant cell with the polynucleotide of claim 1, and (b) regenerating a plant from the transformed plant cell.

12. The polynucleotide of claim 4, wherein the polypeptide is a methionyl-tRNA synthetase.

* * * * *

SEQUENCE LISTING

<160> NUMBER OF SEQ ID NOS: 12

<210> SEQ ID NO 1
<211> LENGTH: 1484
<212> TYPE: DNA
<213> ORGANISM: Zea mays

<400> SEQUENCE: 1

```
tcaaaaacga ctccaggcta gaggggctca tcaagatggc cgatctggtc agttagtccc      60
taatcttcca cctatcttcc ttttttcttt ctcgattgct tactactact tcgaatgcat     120
ttcgaattga ctcacggatt tcctcatcct ctcctgccat gctgctgctg cttggatctg     180
atctgcgcgc caagaccata aacctggccg cgatctgcac gccggccgac tacaacactc     240
gcccactcga caccatctac agcaacttca tcgacgcact cccagtggtc aagtactgct     300
ccgagaacag caagcgtctc atccacttct ccacctgcga ggtctacggc aagaccatcg     360
gcagcttcct ccccaaagac cacccgctcc gcaaggagcc tgaattttat gttcttaaag     420
aagatgagtc gccctgtatt tttggtccaa tcgtgaaaca aagatggtcc tatgcatgcg     480
caaacaact tattgagagg cttgtatttg ctgaaggtgc agaaaatggc cttgatttca     540
caatcgtgag acctttcaat tggattggac caaggatgga cttcattcct ggtgttgatg     600
gtcctagtga aggtgtgcct cgggttttgg cttgcttcag taacaatctg ctccggagag     660
agcccttgaa gcttgttgat gggggtcagt ctcagagaac ctttgtctac atcaaggatg     720
ccatcgaagc tgtagtgctg atgattgaaa atcctgctcg agccaatggc cacatcttca     780
atgttgggaa tccgaacaat gaagttaccg ttagggagtt ggcccaaatg atgacagagg     840
tctacgcaaa tgtctcagga gaggcaccgc tggatgagcc catgattgac gtgagctcga     900
gtcagttcta cggcgaagga tacgatgata gcgacaagag gatccccgac atgactataa     960
tcaacaagca gctaggttgg aacccaaaga cgcctctcaa ggatctgctg gagacaacgc    1020
tgacgtatca gcacaagaca tacaaagaag ctgtgaaaag gcaaatgtcg caggcttcag    1080
cgtcgactta gatagcgtgc ccctggctct cgtctagagc ctagttgcag ctgttaagat    1140
gtttcggaag cgcaggtcac acatacgcta gtgatctttt tttttttgagg ccctagatgt    1200
ccgtgttgtt agataatcaa gggatgctgt atcagtatga tatatttgtg gcagagttga    1260
tgtattccat cgttcgtcgt actagttggg ttggttgccg agagctgtta tatattgctg    1320
tttgagtgta gaactagttg ctcagttata tgttattggt tcatgagatt agcgcccaca    1380
tcaatctgtt gatagcacat acatacatac tatagcaggg caatgctctg ctctgttggt    1440
ttggctccta tgatgaatct cattcgtcag ccatcaagtt tctg                     1484
```

<210> SEQ ID NO 2
<211> LENGTH: 344
<212> TYPE: PRT
<213> ORGANISM: Zea mays

<400> SEQUENCE: 2

```
Ser Leu Ile Phe His Leu Ser Ser Phe Phe Leu Ser Arg Leu Leu Thr
  1               5                  10                  15

Thr Thr Ser Asn Ala Phe Arg Ile Asp Ser Arg Ile Ser Ser Ser Ser
             20                  25                  30

Pro Ala Met Leu Leu Leu Leu Gly Ser Asp Leu Arg Ala Lys Thr Ile
         35                  40                  45
```

```
Asn Leu Ala Ala Ile Cys Thr Pro Ala Asp Tyr Asn Thr Arg Pro Leu
 50                  55                  60

Asp Thr Ile Tyr Ser Asn Phe Ile Asp Ala Leu Pro Val Val Lys Tyr
 65                  70                  75                  80

Cys Ser Glu Asn Ser Lys Arg Leu Ile His Phe Ser Thr Cys Glu Val
                 85                  90                  95

Tyr Gly Lys Thr Ile Gly Ser Phe Leu Pro Lys Asp His Pro Leu Arg
            100                 105                 110

Lys Glu Pro Glu Phe Tyr Val Leu Lys Glu Asp Glu Ser Pro Cys Ile
        115                 120                 125

Phe Gly Pro Ile Val Lys Gln Arg Trp Ser Tyr Ala Cys Ala Lys Gln
    130                 135                 140

Leu Ile Glu Arg Leu Val Phe Ala Glu Gly Ala Glu Asn Gly Leu Asp
145                 150                 155                 160

Phe Thr Ile Val Arg Pro Phe Asn Trp Ile Gly Pro Arg Met Asp Phe
                165                 170                 175

Ile Pro Gly Val Asp Gly Pro Ser Glu Gly Val Pro Arg Val Leu Ala
            180                 185                 190

Cys Phe Ser Asn Asn Leu Leu Arg Arg Glu Pro Leu Lys Leu Val Asp
        195                 200                 205

Gly Gly Gln Ser Gln Arg Thr Phe Val Tyr Ile Lys Asp Ala Ile Glu
    210                 215                 220

Ala Val Val Leu Met Ile Glu Asn Pro Ala Arg Ala Asn Gly His Ile
225                 230                 235                 240

Phe Asn Val Gly Asn Pro Asn Asn Glu Val Thr Val Arg Glu Leu Ala
                245                 250                 255

Gln Met Met Thr Glu Val Tyr Ala Asn Val Ser Gly Glu Ala Pro Leu
            260                 265                 270

Asp Glu Pro Met Ile Asp Val Ser Ser Gln Phe Tyr Gly Glu Gly
        275                 280                 285

Tyr Asp Asp Ser Asp Lys Arg Ile Pro Asp Met Thr Ile Ile Asn Lys
    290                 295                 300

Gln Leu Gly Trp Asn Pro Lys Thr Pro Leu Lys Asp Leu Leu Glu Thr
305                 310                 315                 320

Thr Leu Thr Tyr Gln His Lys Thr Tyr Lys Glu Ala Val Lys Arg Gln
                325                 330                 335

Met Ser Gln Ala Ser Ala Ser Thr
            340

<210> SEQ ID NO 3
<211> LENGTH: 1586
<212> TYPE: DNA
<213> ORGANISM: Oryza sativa

<400> SEQUENCE: 3
gcacgagaga gagtgtgggc gctcttaaat aggagagaaa agaaaaacca ccgccaccga      60
catcgcctcg cctcgtaacc cccaaatcca gcgcctccct tcctcccaa taatcgaatc     120 caatccatct tccacgcgca ttccggatcc gcggaccaag ggaggatgtc gtcgtcgtcg     180
tcgccgcccg ccgcctccgc cgccgcgagg ctggatctgg acggcaaccc catcgcgccc     240
ctcaccatct gcatgatcgg cgccggcggc ttcatcggct cccacctctg cgagaagctc     300
atggccgaga ccgcccacgt cgtctacgcc gtcgacgtct actgcgacaa gatccgccac     360
ctcgtcgacc ccgcccctcc ccacctccat ggccgcatct ccttccaccg cctcaacatc     420
```

-continued

```
aagaacgact ccaggctcga gggcctcatc aagatggccg atctgacgat caacctggcg      480
gcgatctgca cgccggccga ctacaacacg cgccccctcg acaccatcta cagcaacttc      540
atcgacgcgc tccctgtggt caagtactgc tctgagaaca caagcgtct catccacttc      600 tccacgtgcg aggtctacgg caagaccatc ggcagcttcc tccccaccga ccaccctctc      660
cgcaaggaac ctgaatttta tgtactgaaa aagatgaat cccctgcat ttttggtcca       720 attgtgaaac agcgatggtc ttatgcatgt gcgaagcagc ttattgagag cttattttt       780 gctgaaggag cagaaaatgg ccttgagttc acaattgtga acctttcaa ttggattgga       840 ccaagaatgg actttattcc tggtgttgat ggtcctagtg agggtgttcc tcgggttttg      900
gcatgtttca gtaacaatct cctgcgtcgg gagcccctga acttgttga tggtggccag       960 tcccagagaa ctttttgttta cattaaggat gccattgaag ctgttcactt gatgattgaa     1020
aatcctgctc gtgccaatgg tcaaatcttc aatgtcggga atcctaacaa tgaagtcact      1080
gttaggcaat tggctgaaat gatgacagag gtctatgcaa atgtctcagg agagccacca     1140
ctggatgaac ctatgattga cgtgagttcg aagcagttct atggtgaagg atatgatgat     1200
agtgataaga ggattcctga catgaccata atcaacaagc agcttggttg gaatccgaag     1260 accccctctca aggatttgct ggagacaaca ttgacctacc agcacaagac ttacaaagaa     1320
gctatcaaaa ggcaaatgtc acaggcttca gcgtcgagtt agacaacacg ctccaatcca     1380
tagatggtga tgttggctct gtagagcac tgtcagtggc tataatcgtt tggaagtgga     1440
atacgtatac tcaagtaatc ctttttgtgc atctagtcac tcctagatcc ctaccaactt     1500
ttaggtttcc tcctgtgtaa gccggcaagg ggttatccac catatctgtg gcagagtcga     1560
tgtattcatt tgtacctttg gttgct                                          1586
```

<210> SEQ ID NO 4
<211> LENGTH: 427
<212> TYPE: PRT
<213> ORGANISM: Oryza sativa

<400> SEQUENCE: 4

```
Pro Pro Asn Pro Ala Pro Pro Phe Leu Pro Asn Asn Arg Ile Gln Ser
  1               5                  10                  15

Ile Phe His Ala His Ser Gly Ser Ala Asp Gln Gly Arg Met Ser Ser
             20                  25                  30

Ser Ser Ser Pro Pro Ala Ala Ser Ala Ala Ala Arg Leu Asp Leu Asp
         35                  40                  45

Gly Asn Pro Ile Ala Pro Leu Thr Ile Cys Met Ile Gly Ala Gly Gly
     50                  55                  60

Phe Ile Gly Ser His Leu Cys Glu Lys Leu Met Ala Glu Thr Ala His
 65                  70                  75                  80

Val Val Tyr Ala Val Asp Val Tyr Cys Asp Lys Ile Arg His Leu Val
                 85                  90                  95

Asp Pro Ala Pro Pro His Leu His Gly Arg Ile Ser Phe His Arg Leu
            100                 105                 110

Asn Ile Lys Asn Asp Ser Arg Leu Glu Gly Leu Ile Lys Met Ala Asp
        115                 120                 125

Leu Thr Ile Asn Leu Ala Ala Ile Cys Thr Pro Ala Asp Tyr Asn Thr
    130                 135                 140

Arg Pro Leu Asp Thr Ile Tyr Ser Asn Phe Ile Asp Ala Leu Pro Val
145                 150                 155                 160

Val Lys Tyr Cys Ser Glu Asn Asn Lys Arg Leu Ile His Phe Ser Thr
```

-continued

```
                    165                 170                 175
        Cys Glu Val Tyr Gly Lys Thr Ile Gly Ser Phe Leu Pro Thr Asp His
                        180                 185                 190
        Pro Leu Arg Lys Glu Pro Glu Phe Tyr Val Leu Lys Glu Asp Glu Ser
                    195                 200                 205
        Pro Cys Ile Phe Gly Pro Ile Val Lys Gln Arg Trp Ser Tyr Ala Cys
                210                 215                 220
        Ala Lys Gln Leu Ile Glu Arg Leu Ile Phe Ala Glu Gly Ala Glu Asn
        225                 230                 235                 240
        Gly Leu Glu Phe Thr Ile Val Arg Pro Phe Asn Trp Ile Gly Pro Arg
                        245                 250                 255
        Met Asp Phe Ile Pro Gly Val Asp Gly Pro Ser Glu Gly Val Pro Arg
                    260                 265                 270
        Val Leu Ala Cys Phe Ser Asn Asn Leu Leu Arg Arg Glu Pro Leu Lys
                    275                 280                 285
        Leu Val Asp Gly Gly Gln Ser Gln Arg Thr Phe Val Tyr Ile Lys Asp
                290                 295                 300
        Ala Ile Glu Ala Val His Leu Met Ile Glu Asn Pro Ala Arg Ala Asn
        305                 310                 315                 320
        Gly Gln Ile Phe Asn Val Gly Asn Pro Asn Asn Glu Val Thr Val Arg
                        325                 330                 335
        Gln Leu Ala Glu Met Met Thr Glu Val Tyr Ala Asn Val Ser Gly Glu
                    340                 345                 350
        Pro Pro Leu Asp Glu Pro Met Ile Asp Val Ser Ser Lys Gln Phe Tyr
                    355                 360                 365
        Gly Glu Gly Tyr Asp Asp Ser Asp Lys Arg Ile Pro Asp Met Thr Ile
                370                 375                 380
        Ile Asn Lys Gln Leu Gly Trp Asn Pro Lys Thr Pro Leu Lys Asp Leu
        385                 390                 395                 400
        Leu Glu Thr Thr Leu Thr Tyr Gln His Lys Thr Tyr Lys Glu Ala Ile
                        405                 410                 415
        Lys Arg Gln Met Ser Gln Ala Ser Ala Ser Ser
                    420                 425

<210> SEQ ID NO 5
<211> LENGTH: 1338
<212> TYPE: DNA
<213> ORGANISM: Glycine max

<400> SEQUENCE: 5
cgaaggcctc atcaagatgg cagatctcac tattaatctg ctgccatttt gcactcccgc      60
ggattacaac acccgccctc tcgacaccat ttacagcaat tcatcgacg cgctccccgt     120
ggtgaaatac tgttccgaga caacaagcg cctatccat ttctctactt gcgaagtgta     180
cggaaagacg attggagcct tctccctaa agatagtcct cttcgtaagg atccggcata     240
ctatgttctt aaagaagacg agtctccttg cattttggt tctattgaaa acagaggtg     300
gtcttatgcc tgtgcgaaac agttgattga gaggctgatt tatgctgagg gtgctgaaaa     360
tggcttggag ttcacaattg tgaggccttt taactggatt ggacctcgaa tggatttcat     420
tcctggcatt gatggtccaa gtgagggtgt tcctcgggtt cttgcatgct ttagcaataa     480
tcttctcaga ggagagcccc tcaagcttgt ggacggtggc cagtcccaga gaacctttgt     540
ttacattaaa gatgctattg aagctgtctt gctgatgatt gaaaaccctg ccagggccaa     600
tggccacata tttaatgtgg gtaacccaaa caatgaggtt actgttaggc agcttgctga     660
```

```
aataatgatt aaggtttatt caaaggtaag tggcgaacaa actcctgaaa cacctaccgt    720
tgatgtgagc tcaaaagaat tttatggtga gggatatgat gatagtgaca agagaatccc    780
tgacatgacc ataataaaca ggcagcttgg atggaatccc aagacttcac tttgggacct    840
gcttgagtcc actctgacat atcagcacag gacatatgct gaagccgtta agaaagtcat    900
tgcaaaaccc gttgcaagtt aagcttttta cagtgatggt gatgtgctac ctttgagaag    960
ggtgttcttg tcttgcccaa gtgttctgcc atattatact ggttgatttt atataaaatc   1020
gtaaattttc ctcctattgg tttcgttagc ctgtaggcaa tatagccccc acatggagaa   1080
gtaggaattt atacaagggc aatctgtgct ctatgtaatt ttaatgtaga gaccatgcgc   1140
tgctaaacat gttgagacac tttatatatt acctagggaa gacttttttc tgtgttttta   1200
aggatctctc gattcattgc tttgttgtct ttccaggtca gctgtaagtt gtatcattct   1260
atcattctgt ttgaccttaa gccatgtgtt ctaaattatt gtcattaatt tattttatga   1320
atattttttt ttgttact                                                 1338
```

<210> SEQ ID NO 6  
<211> LENGTH: 306  
<212> TYPE: PRT  
<213> ORGANISM: Glycine max

<400> SEQUENCE: 6

```
Glu Gly Leu Ile Lys Met Ala Asp Leu Thr Ile Asn Leu Ala Ala Ile
 1               5                  10                  15

Cys Thr Pro Ala Asp Tyr Asn Thr Arg Pro Leu Asp Thr Ile Tyr Ser
            20                  25                  30

Asn Phe Ile Asp Ala Leu Pro Val Val Lys Tyr Cys Ser Glu Asn Asn
        35                  40                  45

Lys Arg Leu Ile His Phe Ser Thr Cys Glu Val Tyr Gly Lys Thr Ile
    50                  55                  60

Gly Ala Phe Leu Pro Lys Asp Ser Pro Leu Arg Lys Asp Pro Ala Tyr
65                  70                  75                  80

Tyr Val Leu Lys Glu Asp Ser Pro Cys Ile Phe Gly Ser Ile Glu
                85                  90                  95

Lys Gln Arg Trp Ser Tyr Ala Cys Ala Lys Gln Leu Ile Glu Arg Leu
            100                 105                 110

Ile Tyr Ala Glu Gly Ala Glu Asn Gly Leu Glu Phe Thr Ile Val Arg
        115                 120                 125

Pro Phe Asn Trp Ile Gly Pro Arg Met Asp Phe Ile Pro Gly Ile Asp
    130                 135                 140

Gly Pro Ser Glu Gly Val Pro Arg Val Leu Ala Cys Phe Ser Asn Asn
145                 150                 155                 160

Leu Leu Arg Gly Glu Pro Leu Lys Leu Val Asp Gly Gly Gln Ser Gln
                165                 170                 175

Arg Thr Phe Val Tyr Ile Lys Asp Ala Ile Glu Ala Val Leu Leu Met
            180                 185                 190

Ile Glu Asn Pro Ala Arg Ala Asn Gly His Ile Phe Asn Val Gly Asn
        195                 200                 205

Pro Asn Asn Glu Val Thr Val Arg Gln Leu Ala Glu Ile Met Ile Lys
    210                 215                 220

Val Tyr Ser Lys Val Ser Gly Glu Gln Thr Pro Glu Thr Pro Thr Val
225                 230                 235                 240

Asp Val Ser Ser Lys Glu Phe Tyr Gly Glu Gly Tyr Asp Asp Ser Asp
```

-continued

```
                245                 250                 255
Lys Arg Ile Pro Asp Met Thr Ile Ile Asn Arg Gln Leu Gly Trp Asn
            260                 265                 270

Pro Lys Thr Ser Leu Trp Asp Leu Leu Glu Ser Thr Leu Thr Tyr Gln
        275                 280                 285

His Arg Thr Tyr Ala Glu Ala Val Lys Lys Val Ile Ala Lys Pro Val
    290                 295                 300

Ala Ser
305

<210> SEQ ID NO 7
<211> LENGTH: 664
<212> TYPE: DNA
<213> ORGANISM: Triticum aestivum

<400> SEQUENCE: 7
gcacgagcaa caatctcctc cgtagagagc ccctgaagct tgtcgatggc ggcgagtccc      60
agagaacttt tgtttacatc aaggatgcca ttgaagctgt tcttctgatg attgaaaacc     120
ctgctcgagc caatggtcat atcttcaacg ttgggaaccc cgacaatgaa gtcactgtta     180
gggagttggc cgaaatgatg acagaggtct acgctaaggt ctcaggagag cccccgctgg     240
aggagcctgt ggtcgacgtg agcgcgaaag aattctacgg cgaagggtac gacgacagcg     300
acaagaggat ccctgacatg accctgatca caagcagct aggtggaaac cccaagaccc     360
ctctcaagga cctgctggag acgacgctga cctaccagca aagacctac aaggaggctg     420
tgaagacgca gatgtgtctg gccacggcga cgccttcaag ctagacgatg acggcgcggc     480
catgctgctc ttgatctttt ggaagccaga tactatatc gtagtgaaac cgtcgtcgtc     540
gttttttgtcg cgcctctaga tcacacccac ccatcttctt acctacctag attcgtcatt     600
gtgtaaccct atattgggca aagggaactg agtatctatt atacctgtgg tggcagtgtt     660
tgtt                                                                    664

<210> SEQ ID NO 8
<211> LENGTH: 153
<212> TYPE: PRT
<213> ORGANISM: Triticum aestivum

<400> SEQUENCE: 8

Thr Ser Asn Asn Leu Leu Arg Arg Glu Pro Leu Lys Leu Val Asp Gly
  1               5                  10                  15

Gly Glu Ser Gln Arg Thr Phe Val Tyr Ile Lys Asp Ala Ile Glu Ala
             20                  25                  30

Val Leu Leu Met Ile Glu Asn Pro Ala Arg Ala Asn Gly His Ile Phe
         35                  40                  45

Asn Val Gly Asn Pro Asp Asn Glu Val Thr Val Arg Glu Leu Ala Glu
     50                  55                  60

Met Met Thr Glu Val Tyr Ala Lys Val Ser Gly Glu Pro Pro Leu Glu
 65                  70                  75                  80

Glu Pro Val Val Asp Val Ser Ala Lys Glu Phe Tyr Gly Glu Gly Tyr
                 85                  90                  95

Asp Asp Ser Asp Lys Arg Ile Pro Asp Met Thr Leu Ile Asn Lys Gln
            100                 105                 110

Leu Gly Trp Asn Pro Lys Thr Pro Leu Lys Asp Leu Leu Glu Thr Thr
        115                 120                 125

Leu Thr Tyr Gln His Lys Thr Tyr Lys Glu Ala Val Lys Thr Gln Met
```

```
                130                 135                 140
Cys Leu Ala Thr Ala Thr Pro Ser Ser
145                 150

<210> SEQ ID NO 9
<211> LENGTH: 2281
<212> TYPE: DNA
<213> ORGANISM: Zea mays

<400> SEQUENCE: 9
ccacgcgtcc gaaaatttt  tagctgatag gcttgttgaa ggaacatgcc cgaacaaagt    60
ctgcaacgca tcagcaagag gagatcagtg tgaaacatgc agcaccttgt tgaatccaac   120
tgaacttatt gacccaaagt gcaaggtttg taagaacact ccacgtattc gtgacacgga   180
tcacttattt ttggagcttc ctctattgag agacaagctg gtaaactaca tcaatgaaac   240
ttcagttgct ggtttgtgga gtcaaaatgc tattcaagca acaaatgcat ggctgaagga   300
agggctaaag ccacgctgca tcaccagaga tcttaaatgg ggtgttcctg tcccccatga   360
gaagtataaa gacaaggtgt tctatgtttg gtttgatgca cctatcggct acgtgtctat   420
tacggcatcc tatacacctg agtgggagaa gtggtggaag aatcctgata atgtagaatt   480
gtttcagttt atgggcaaag ataatgtgcc gtttcacacg atcatgttcc cttcaacgct   540
actcggaact ggggaaaagt ggacaatgat gaaaacgata agtgttactg aatatttgaa   600
ttatgaagca ggcaaatttt ccaagagtaa aggtattgga gtctttggta atgatgcaaa   660
ggatacaaat attcctcctg aagtatggcg atactatttg cttatgaatc gccctgaggc   720
atcagataca ctctttactt gggctgattt gcaagcccaa ttgaacagcg agttgctgaa   780
caacttggga aacttcatta atcgtgtgct aagttttgtt gcaaaaccag ctggagctgg   840
atatggttct gttgtacccg atgcacctaa tgcgggcgcg cacacattga caaaaacact   900
tgcagaaaaa accagtaaat gggttgaaca atatctcgac gcaatggaaa aggttaaact   960
gaaacaagga ctcaagagtg caatgggcat ttctagtgat ggaaatgcat atttgcaaga  1020
gagccagttt tggaaacttt acaaggaaga tcctgcagca tgtgcaatcg tgatgaaaac  1080
ttcagttggc cttgtttacc tgcttgcctg tctgctggag cctttcatgc cctcttttc  1140
tgatgaagtg ttacgtcaac taaatttatc tccagaagaa aatctgtcat taagtgaaga  1200
aaagggagaa attgcgaagg caaaaactcc ttggaatttt gtaccagcag gtcacagaat  1260
agggaaaccc gcacctctgt tcaaggaatt gaaagatgaa gacgtagctc tccatagaga  1320
aaaatatgca gggagtcaag ctgagagaag ctcaaaagca gcagctgatg ctgaagccaa  1380
caaagttgct aaccagctca agggcacaaa attatctgat ggaggaacaa aaaaggaacc  1440
gaagaaacaa tctggtggct caaaatcgaa gacagctgag gctgacatta cagttgcaaa  1500
gttggatatt agagtggggc ttatcagaaa agcagagaag catccagatg ctgattccct  1560
ttacgtggag gagattgatg ttggagagga cgcgccgaga acagtagtca gtggccttgt  1620
taaattcata cctcttgaag aaatgcagag ccggaaagtt tgcgtgctct gcaatctgaa  1680
accggtggca atgcgtggca taaaatcaca tgcaatggtt ctggctgcat cgaatgagga  1740
ccacacgaag gttgagttgg tggaacctcc agagtctgct gctgtggggg agcgtgttac  1800
cttttgctggg tacgcgggtg agcccgaggc ttccctcagt ggcaagagca agacgtggga  1860
gaagcttgcc gccgagttgc acagcaacgg tgagctggtg gcgtgctaca gagatgtgcc  1920
cttcactacc tcggctggag tctgcagggt gaagacaata gcgaacggag agattcgcta  1980
```

-continued

```
gtaccacatc accgaactgc agccagctga gccggtctgt gtctggtttc gctgaaagcg    2040
attgttcctg actttcatct tcgaaaattt tggtatttcc atttgttcaa ataccgcaaa    2100
gcaaccatga tttagaaaaa tacagagagt gcccttctg catcctcttt ttatcagtta     2160
gtacttggct cctgtcgtct cactcggagg ctccatgctt cttgctgtat ctgtatttcc    2220
ttagaagtga ttctttacct gctcttattt atagttccat atgaaaggaa caaagtgtat    2280
c                                                                    2281
```

<210> SEQ ID NO 10
<211> LENGTH: 659
<212> TYPE: PRT
<213> ORGANISM: Zea mays

<400> SEQUENCE: 10

```
His Ala Ser Glu Lys Phe Leu Ala Asp Arg Leu Val Glu Gly Thr Cys
 1               5                  10                  15

Pro Asn Lys Val Cys Asn Ala Ser Ala Arg Gly Asp Gln Cys Glu Thr
             20                  25                  30

Cys Ser Thr Leu Leu Asn Pro Thr Glu Leu Ile Asp Pro Lys Cys Lys
         35                  40                  45

Val Cys Lys Asn Thr Pro Arg Ile Arg Asp Thr Asp His Leu Phe Leu
     50                  55                  60

Glu Leu Pro Leu Leu Arg Asp Lys Leu Val Asn Tyr Ile Asn Glu Thr
 65                  70                  75                  80

Ser Val Ala Gly Leu Trp Ser Gln Asn Ala Ile Gln Ala Thr Asn Ala
                 85                  90                  95

Trp Leu Lys Glu Gly Leu Lys Pro Arg Cys Ile Thr Arg Asp Leu Lys
            100                 105                 110

Trp Gly Val Pro Val Pro His Glu Lys Tyr Lys Asp Lys Val Phe Tyr
        115                 120                 125

Val Trp Phe Asp Ala Pro Ile Gly Tyr Val Ser Ile Thr Ala Ser Tyr
    130                 135                 140

Thr Pro Glu Trp Glu Lys Trp Trp Lys Asn Pro Asp Asn Val Glu Leu
145                 150                 155                 160

Phe Gln Phe Met Gly Lys Asp Asn Val Pro Phe His Thr Ile Met Phe
                165                 170                 175

Pro Ser Thr Leu Leu Gly Thr Gly Glu Lys Trp Thr Met Met Lys Thr
            180                 185                 190

Ile Ser Val Thr Glu Tyr Leu Asn Tyr Glu Ala Gly Lys Phe Ser Lys
        195                 200                 205

Ser Lys Gly Ile Gly Val Phe Gly Asn Asp Ala Lys Asp Thr Asn Ile
    210                 215                 220

Pro Pro Glu Val Trp Arg Tyr Tyr Leu Leu Met Asn Arg Pro Glu Ala
225                 230                 235                 240

Ser Asp Thr Leu Phe Thr Trp Ala Asp Leu Gln Ala Lys Leu Asn Ser
                245                 250                 255

Glu Leu Leu Asn Asn Leu Gly Asn Phe Ile Asn Arg Val Leu Ser Phe
            260                 265                 270

Val Ala Lys Pro Ala Gly Ala Gly Tyr Gly Ser Val Val Pro Asp Ala
        275                 280                 285

Pro Asn Ala Gly Ala His Thr Leu Thr Lys Thr Leu Ala Glu Lys Thr
    290                 295                 300

Ser Lys Trp Val Glu Gln Tyr Leu Asp Ala Met Glu Lys Val Lys Leu
305                 310                 315                 320
```

```
Lys Gln Gly Leu Lys Ser Ala Met Gly Ile Ser Ser Asp Gly Asn Ala
                325                 330                 335

Tyr Leu Gln Glu Ser Gln Phe Trp Lys Leu Tyr Lys Glu Asp Pro Ala
            340                 345                 350

Ala Cys Ala Ile Val Met Lys Thr Ser Val Gly Leu Val Tyr Leu Leu
        355                 360                 365

Ala Cys Leu Leu Glu Pro Phe Met Pro Ser Phe Ser Asp Glu Val Leu
    370                 375                 380

Arg Gln Leu Asn Leu Ser Pro Glu Glu Asn Leu Ser Leu Ser Glu Glu
385                 390                 395                 400

Lys Gly Glu Ile Ala Lys Ala Lys Thr Pro Trp Asn Phe Val Pro Ala
                405                 410                 415

Gly His Arg Ile Gly Lys Pro Ala Pro Leu Phe Lys Glu Leu Lys Asp
            420                 425                 430

Glu Asp Val Ala Leu His Arg Glu Lys Tyr Ala Gly Ser Gln Ala Glu
        435                 440                 445

Arg Ser Ser Lys Ala Ala Ala Asp Ala Glu Ala Asn Lys Val Ala Asn
450                 455                 460

Gln Leu Lys Gly Thr Lys Leu Ser Asp Gly Gly Thr Lys Lys Glu Pro
465                 470                 475                 480

Lys Lys Gln Ser Gly Gly Ser Lys Ser Lys Thr Ala Glu Ala Asp Ile
                485                 490                 495

Thr Val Ala Lys Leu Asp Ile Arg Val Gly Leu Ile Arg Lys Ala Glu
            500                 505                 510

Lys His Pro Asp Ala Asp Ser Leu Tyr Val Glu Glu Ile Asp Val Gly
        515                 520                 525

Glu Asp Ala Pro Arg Thr Val Val Ser Gly Leu Val Lys Phe Ile Pro
    530                 535                 540

Leu Glu Glu Met Gln Ser Arg Lys Val Cys Val Leu Cys Asn Leu Lys
545                 550                 555                 560

Pro Val Ala Met Arg Gly Ile Lys Ser His Ala Met Val Leu Ala Ala
                565                 570                 575

Ser Asn Glu Asp His Thr Lys Val Glu Leu Val Glu Pro Pro Glu Ser
            580                 585                 590

Ala Ala Val Gly Glu Arg Val Thr Phe Ala Gly Tyr Ala Gly Glu Pro
        595                 600                 605

Glu Ala Ser Leu Ser Gly Lys Ser Lys Thr Trp Glu Lys Leu Ala Ala
    610                 615                 620

Glu Leu His Ser Asn Gly Glu Leu Val Ala Cys Tyr Arg Asp Val Pro
625                 630                 635                 640

Phe Thr Thr Ser Ala Gly Val Cys Arg Val Lys Thr Ile Ala Asn Gly
                645                 650                 655

Glu Ile Arg

<210> SEQ ID NO 11
<211> LENGTH: 469
<212> TYPE: DNA
<213> ORGANISM: Glycine max
<220> FEATURE:
<221> NAME/KEY: unsure
<222> LOCATION: (416)
<220> FEATURE:
<221> NAME/KEY: unsure
<222> LOCATION: (468)

<400> SEQUENCE: 11
```

```
                                                    -continued gtttgatgct ttactaggct atatatcagc actatctgat gatcaggaac aacctgattt      60
acttaaaact gtttcttcag gttggccagc ttcactgcac ttgattggta aggatattct     120
acgcttccat gctgtttact ggccagctat gctaatgtct gctggactaa gccttcctaa     180
aatggtattt ggccatggat tcttgacaaa ggatggaatg aagatgggca agtcactagg     240
gaatatactt gaaccaaacg atttggttaa taaatttggg acagatgcag ttagatactt     300
cttcctcaga gaggtggaat ttggcaatga tggagactat tcagaggaac gcttcatcaa     360
tattgtgaat gcacatcttg ccaatacaat tggaaatctt cttaatcgga cactangact     420
tctgaaaaag aactgccaat caattctggt ggtggatcca ctacagcng                 469

<210> SEQ ID NO 12
<211> LENGTH: 152
<212> TYPE: PRT
<213> ORGANISM: Glycine max
<220> FEATURE:
<221> NAME/KEY: UNSURE
<222> LOCATION: (139)

<400> SEQUENCE: 12

Phe Asp Ala Leu Leu Gly Tyr Ile Ser Ala Leu Ser Asp Asp Gln Glu
 1               5                  10                  15

Gln Pro Asp Leu Leu Lys Thr Val Ser Ser Gly Trp Pro Ala Ser Leu
             20                  25                  30

His Leu Ile Gly Lys Asp Ile Leu Arg Phe His Ala Val Tyr Trp Pro
         35                  40                  45

Ala Met Leu Met Ser Ala Gly Leu Ser Leu Pro Lys Met Val Phe Gly
     50                  55                  60

His Gly Phe Leu Thr Lys Asp Gly Met Lys Met Gly Lys Ser Leu Gly
 65                  70                  75                  80

Asn Ile Leu Glu Pro Asn Asp Leu Val Asn Lys Phe Gly Thr Asp Ala
                 85                  90                  95

Val Arg Tyr Phe Phe Leu Arg Gly Val Glu Phe Gly Asn Asp Gly Asp
            100                 105                 110

Tyr Ser Glu Glu Arg Phe Ile Asn Ile Val Asn Ala His Leu Ala Asn
        115                 120                 125

Thr Ile Gly Asn Leu Leu Asn Arg Thr Leu Xaa Leu Leu Lys Lys Asn
    130                 135                 140

Cys Gln Ser Ile Leu Val Val Asp
145                 150
```